(12) United States Patent
Milbocker

(10) Patent No.: US 9,339,583 B2
(45) Date of Patent: *May 17, 2016

(54) IN SITU BONDS

(71) Applicant: Promethean Surgical Devices, LLC, East Hartford, CT (US)

(72) Inventor: Michael T. Milbocker, Holliston, MA (US)

(73) Assignee: Promethean Surgical Devices, LLC, East Hartford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/934,831

(22) Filed: Jul. 3, 2013

(65) Prior Publication Data

US 2013/0296460 A1    Nov. 7, 2013

Related U.S. Application Data

(63) Continuation of application No. 10/020,331, filed on Dec. 12, 2001, now Pat. No. 8,501,165.

(51) Int. Cl.
| | |
|---|---|
| *A61L 24/04* | (2006.01) |
| *C08G 18/10* | (2006.01) |
| *C08G 18/12* | (2006.01) |
| *C08G 18/48* | (2006.01) |
| *C08G 18/66* | (2006.01) |
| *C08G 18/75* | (2006.01) |
| *C08G 18/30* | (2006.01) |
| *C09J 175/04* | (2006.01) |

(52) U.S. Cl.
CPC ............... *A61L 24/046* (2013.01); *C08G 18/10* (2013.01); *C08G 18/12* (2013.01); *C08G 18/4812* (2013.01); *C08G 18/4837* (2013.01); *C08G 18/6677* (2013.01); *C08G 18/755* (2013.01); *C09J 175/04* (2013.01); *C08G 2210/00* (2013.01)

(58) Field of Classification Search
CPC ...... A61K 31/74; A61K 9/0024; A61L 31/10; A61L 27/34; A61L 24/046; C08G 18/10; C08G 18/12; C08G 18/4812; C08G 18/4854; C08G 18/4833; C08G 18/4858; C08G 18/4829; C08G 18/302; C08G 18/755; C08G 2210/00; C08G 18/6677; C08G 18/4837; C09J 175/04
USPC ........ 424/422, 78.08, 78.17, 78, 37; 523/118; 560/358
See application file for complete search history.

(56) References Cited

U.S. PATENT DOCUMENTS

| | | | |
|---|---|---|---|
| 3,939,123 A | 2/1976 | Matthews et al. | |
| 4,118,354 A | 10/1978 | Harada et al. | |
| 4,241,537 A * | 12/1980 | Wood .................... | A01G 9/1086 47/56 |
| 4,577,631 A | 3/1986 | Kreamer | |
| 4,731,410 A | 3/1988 | Bueltjer et al. | |
| 4,798,876 A * | 1/1989 | Gould ..................... | A61L 27/26 525/454 |
| 4,806,614 A * | 2/1989 | Matsuda ................ | A61L 24/046 528/59 |
| 4,829,099 A * | 5/1989 | Fuller .................... | A61L 24/046 523/111 |
| 4,898,919 A | 2/1990 | Ueda et al. | |
| 4,966,953 A | 10/1990 | Shikinami et al. | |
| 5,156,613 A | 10/1992 | Sawyer | |
| 5,169,720 A * | 12/1992 | Braatz et al. ............. | 428/423.1 |
| 5,209,776 A | 5/1993 | Bass et al. | |
| 5,430,072 A | 7/1995 | Muller et al. | |
| 5,445,597 A | 8/1995 | Clark et al. | |
| 5,461,124 A | 10/1995 | Ritter et al. | |
| 5,468,804 A | 11/1995 | Schmalstieg et al. | |
| 5,487,897 A | 1/1996 | Polson | |
| 5,508,111 A | 4/1996 | Schmucker | |
| 5,571,117 A | 11/1996 | Ahn | |
| 5,634,931 A | 6/1997 | Kugel | |
| 5,813,975 A | 9/1998 | Valenti | |
| 5,817,303 A | 10/1998 | Stedronsky et al. | |
| 5,821,275 A | 10/1998 | Madan et al. | |
| 5,866,632 A | 2/1999 | Hashimoto et al. | |
| 5,925,781 A | 7/1999 | Pantone et al. | |
| 5,972,007 A | 10/1999 | Sheffield et al. | |
| 6,033,654 A | 3/2000 | Stedronsky et al. | |
| 6,162,863 A | 12/2000 | Ramalingam | |
| 6,191,216 B1 | 2/2001 | Ganster | |
| 6,197,036 B1 | 3/2001 | Tripp et al. | |
| 6,211,335 B1 | 4/2001 | Owen | |
| 6,322,492 B1 | 11/2001 | Kovac | |
| 6,334,446 B1 | 1/2002 | Beyar | |
| 6,376,698 B1 | 4/2002 | Bleys | |
| 6,423,333 B1 | 7/2002 | Stedronsky et al. | |
| 6,502,578 B2 | 1/2003 | Raz et al. | |

(Continued)

FOREIGN PATENT DOCUMENTS

| | | |
|---|---|---|
| EP | 0390481 A2 | 3/1990 |
| WO | WO 02/26848 A2 | 4/2002 |

OTHER PUBLICATIONS

Debnath, P. et al., Journal of Chemical Physics 2003, 118(9): 1970-1978.

(Continued)

*Primary Examiner* — Blessing M Fubara

(74) *Attorney, Agent, or Firm* — Mannava & Kang, P.C.; Carol L. Bunner

(57) ABSTRACT

A biocompatible tissue-bonding adhesive composition having a polyol of functionality N. The polyol being terminated has at least one polyisocyanate in solution with at least (N−1)% of the solution having free polyisocyanate. N may be in the range 1.5-8. The polyol may be a branched polypropylene/polyethylene oxide copolymer.

15 Claims, No Drawings

(56) References Cited

U.S. PATENT DOCUMENTS

| | | | |
|---|---|---|---|
| 6,503,190 B1 | 1/2003 | Ulmsten et al. | |
| 6,524,327 B1 * | 2/2003 | Spacek | C08G 18/10 606/214 |
| 6,528,577 B2 | 3/2003 | Isozaki et al. | |
| 6,562,932 B1 | 5/2003 | Markushch et al. | |
| 6,589,269 B2 | 7/2003 | Zhu et al. | |
| 6,610,779 B1 | 8/2003 | Blum et al. | |
| 6,630,050 B1 | 10/2003 | Moeller et al. | |
| 6,645,137 B2 | 11/2003 | Ulmsten et al. | |
| 6,652,595 B1 | 11/2003 | Nicolo | |
| 6,669,654 B2 | 12/2003 | Diokno et al. | |
| 6,818,018 B1 | 11/2004 | Sawhney | |
| 8,501,165 B2 * | 8/2013 | Molbocker | 424/78.17 |
| 2003/0083642 A1 | 5/2003 | Boyd et al. | |
| 2004/0170597 A1 | 9/2004 | Beckman et al. | |
| 2009/0324675 A1 * | 12/2009 | Gunatillake et al. | 424/423 |

OTHER PUBLICATIONS

McKetta J. J. et al., Encyclopedia of Chemical Processing and Design 1992, vol. 41, pp. 32, 33, and 43-45, Marcel Dekker, Inc., NY.

Hiemenz, P. C., Polymer Chemistry 1984, pp. 12, 433-434, Marcel Dekker, Inc., NY.

* cited by examiner

IN SITU BONDS

BACKGROUND OF THE INVENTION

1. Field of the Invention

This invention relates to synthetic surgical adhesives/sealants and tissue bonds created by reacting the adhesive with living mammalian tissue, and more specifically, to a tissue cross-linking pre-polymer for the purpose of forming a tissue crosslinked bond. This application also claims priority to U.S. application Ser. No. 10/020,331, filed on Dec. 12, 2001, now allowed, the disclosure of which is hereby incorporated by reference.

2. Prior Art

U.S. Pat. No. 4,806,614, Matsuda et al describes a method for surgical bonding of tissue, which comprises applying thereto a surgical adhesive consisting essentially of at least one NCO-terminated hydrophilic urethane prepolymer, derived from at least one organic polyisocyanate and a polyol component comprising at least one hydrophilic polyether polyol having an oxyethylene content of at least 30%.

In the present invention, the hydrogen peroxide pretreatment is replaced with an organic polyisocyanate treatment. The treatment is achieved when excess polyisocyanate is added to the prepolymer. This modification creates a 1-part formulation that bonds tissue upon contact. This excess is critical, compositions without free polyisocyanate form mechanical rather than covalent bonds that are susceptible to swell and differential motion between tissue and the cured adhesive. Therefore, U.S. Pat. No. 4,806,614 does not achieve a covalent bond with tissue.

The triol nature of the adhesive is also very important. Surgical adhesives without trifunctional or branched structure will not bond tissue. This feature is not taught in U.S. Pat. No. 4,806,614.

The formation of a hydrated bond is critical in surgical environments. Most polyurethane prepolymers, and in particular those taught in U.S. Pat. No. 4,806,614, will not form hydrogels due to the lack of the use of a trifunctional additive in the reaction mix. We have found that polyurethane prepolymers that do not form hydrogels do not make strong bonds to tissue, and cross link internally rather than bonding to tissue.

The examples of U.S. Pat. No. 4,806,614 site p-phenylene diisocyanate, which is not reactive enough to form strong tissue bonds. Those with TDI (Toluene Diisocyanate) do not have the proper PEO/PPO (polyethylene oxide/polypropylene oxide) ratio to form hydrogels. The examples given and the text illustrate that a hydrogel formation was not a goal of U.S. Pat. No. 4,806,614. U.S. Pat. No. 4,806,614 does not teach formation of a hydrogel with 30-90% water. Devices of the type given in U.S. Pat. No. 4,806,614 will take up about 10% water.

U.S. Pat. No. 4,806,614 does not teach a covalent bond, or the necessity of tissue or bodily fluids to bond formation. U.S. Pat. No. 4,806,614 may disclose the achieving of hemostasis through mechanical bonding but this teaching will not achieve useful levels of durability resulting from covalent bonding, nor will the desired level of flexibility and biocompatibility be achieved without hydrogel formation.

Since U.S. Pat. No. 4,806,614 refers to addition of cyanoacrylic compounds, defined in the text as "cyano groups", this represents a further divergence from the object of producing desired "hydrated" bonds, particularly since such compounds exclude water. Such formulation of this prior art has been found to self-polymerize before forming a bond with tissue.

The present invention achieves bonding success through the orchestration of three polymerization pathways. One, the free polyisocyanate bonds to tissue. The free polyisocyanate bonds first to tissue because it is more mobile (lower molecular weight) than the NCO terminated polyol. This feature prevents competition between bulk polymerization and tissue bonding. Two, the NCO terminated polyol bonds to the free polyisocyanate or amine on the tissue interface. Three, the NCO terminated polyol bonds amongst itself to form bulk adhesive strength and collects remaining unreacted free polyisocyanate or polyamine (a safety feature). The polyamine is formed by reaction of polyisocyanate with water. The order of this cascade is critical and is determined by 1) the presence of free polyisocyanate, 2) the reactivity of the free polyisocyanate, 3) the molecular weight of the polyol, 4) the trifunctionality of the polyol, 5) protein initiated polymerization and the location of that reaction, and 6) water initiated polymerization and the diffusion direction of the water. None of this is taught in U.S. Pat. No. 4,806,614.

U.S. Pat. No. 5,457,147 (McGrath et al.) describes a process for the formation of poly(secondary amine) comprising units of

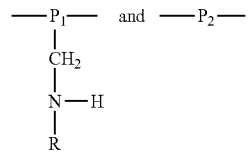

wherein $P_1$ represents the repeating unit of a polymer containing olefinic unsaturation which has been hydroformylated and reductively aminated. $P_2$ represents the repeating unit of the same polymer containing olefinic unsaturation having reactive carbon-carbon double bonds. R is selected from the group consisting of aliphatic, aromatic, cycloaliphatic, substituted aliphatic, aromatic and cycloaliphatic groups and combinations thereof, and the ratio of $P_1$ to $P_2$ is about 1:99 to about 90:10. The U.S. Pat. No. 5,457,147 refers to amines of a particular structure, and more generally to processes for creating such amines. This patent does not teach or relate to tissue bonds. The amines formed by the reaction of the adhesive of the present invention with tissue which forms the bond, is not taught by the '147 patent since the tissue portion of the '147 patent is not a repeating unit polymer containing olefinic unsaturation. Furthermore, the amines discussed in the '147 patent require the metal catalysts primarily concerned with controlling functional density. The hydroformylation reaction is conducted under a monoxide/hydrogen atmosphere at a high pressure. The processes are not useful in the formation of tissue bonds.

U.S. Pat. No. 5,173,301 (Itoh, Matsuda) relates to prepolymers formed of polyester polyol derived from dicarboxylic acid. The polyester polyol of this reference will not create a hydrogel, nor a suitably flexible polymer. The fluorinated diisocyanate will self-polymerize before creating a useful tissue bond. Furthermore, the excess polyisocyanate of the present invention is not present. Halogens figure prominently in the text, and although they reportedly provide enhanced biocompatibility, the present inventor's experience with fluorine containing diisocyanates has indicated that they tend to transform significantly during storage. In general, the compositions of the teachings in the '301 are likely to be unstable and transform during both storage and irradiation sterilization.

One of the primary goals of the '301 was to create a biodegradable formulation, but by sacrificing its bond strength. Biodegradable formulations are created in the present invention by increasing the EO (ethylene oxide) content.

Example 1 (in the '614 patent) particularly illuminates the difficulty in striking a balance between bond effectiveness and degradability. A hybrid consisting of a degradable polyol and a PEO-PPO polymer is reacted with FHDI, a fluorinated diisocyanate. The PEO-PPO polymer provides strength and the polyester component provides the points of degradation.

U.S. Pat. No. 4,994,542 (Matsuda et al) is very similar to '614 except that the fluorinated polyisocyanate as a more biocompatible isocyanate is introduced. Claim 2 in particular teaches fluorine-containing aliphatic polyisocyanates.

U.S. Pat. No. 5,578,662 (Bennett et al) describes a bioabsorbable composition comprising a branched copolymer containing a major amount of alkylene oxide units and a minor amount of units derived from a bioabsorbable monomer, the copolymer being terminated with at least one lysine isocyanate group. The '662 focuses on bioabsorbable implantable compositions. It mentions its use as a surgical adhesive or a bone putty. It does not patent the composition comprising a prepolymer, bodily fluids, and tissue—all of which are required to form a tissue bond. The text defines the type of surgical adhesive: "The cross-linked star polymers are useful for example as bone adhesives or bone fillers (p.5)". References to surgical adhesives are made nowhere else in the body of the patent. It does not describe a covalent bond to tissue. It does not discuss the need, or indicate in any claim the presence of free polyisocyanate. Furthermore, the compositions disclosed in '662 are viscous and better described as "putty". These reasons suggest that the compositions are unsuitable as tissue adhesives.

Furthermore, claim 1 of the '662 patent is very specific about the type of isocyanate to be used although the text is more general. Claim 1 is not particular about the isocyanate being poly-functional, although the text discusses difunctional alternatives. The absence of a poly-functional specification and the absence of a catalytic formation of amine by reaction of free polyiscyanate with water leads to the conclusion that claim 1 of the '662 patent does not relate to tissue adhesives, except insofar as being a component. Such a composition would have minimal tissue bonding capability.

The type of isocyanate specified in the '062 patent will likely require a catalyst to be effective as a tissue adhesive. For example, in the text it states, "Cross-linking is normally performed by exposing the terminated polymer to water in the presence of a catalyst, such as a tertiary amine". It does not teach in the text nor does it specify in the claims the use of an excess for polyisocyanate and its interaction with body fluids to produce the necessary amine. It is not specified in the text or in the claims what fraction of the star molecule's arms are terminated. This specification is critical to ensure propagation of tissue interpenetrating structures, and in the absence of further teaching would favor self-polymerization over crosslinking to tissue structures.

There is some question as to whether the composition of claim 1 is bioabsorbable since the minor component is bioabsorbable, and the polyfunctional aspects of the alkylene oxide units may produce sufficient cross linking to prevent dissolution of the cured composition. The text of the '062 patent teaches away from surgical adhesives stating, "It has been discovered that novel polymers in accordance with this disclosure can serve as a substrate for cell growth. Specifically, star polymers terminated with lysine diisocyanate, with or without an induced charge, can be used as a cell growth substrate." The text further teaches away from a surgical adhesive by citing applications of the composition recited in claim 1 that are nonfunctional with respect to the isocyanate, " . . . one or more medico-surgically useful substances, e.g., those which accelerate or beneficially modify the healing process when particles are applied to a surgical repair, can be incorporated into surgical devices made from materials described herein . . . . " The text thus strongly suggests that the composition recited is to be used as a delivery device for therapeutics in its cured or cross-linked state, not as a tissue adhesive. The text also does not link isocyanate reactivity to the composition's ability to deliver therapeutics.

All of the examples use a catalyst, Sn(Oct) which is toxic and not acceptable for use in the manufacture of medical devices. The present invention achieves its composition without the use of catalysts and specifically teaches away from their use. Furthermore, the composition of the '062 patent could not be manufactured without the use of these catalysts since the arms of the star molecule would likely sterically hinder arm termination by isocyanate.

Finally, the abstract and text of the '062 patent suggests the composition taught is fully crosslinked before its use in the body. For example, "The star polymers can be terminated with isocyanate, mixed with a filler and/or cross-linked." It appears that the reference of its teachings as a surgical adhesive is restricted to those substances that are tacky or mechanically adhesive and non-functional with respect to the isocyanate.

In summary, several absorbable compositions are in the public domain. For example, U.S. Pat. No. 4,132,839 covers hydroxy carboxylic acid based compositions and. U.S. Pat. No. 4,049,592 covers isocyanate terminated hydroxyester polyol based compositions. These compositions are meant to be included in the family of absorbable 1-part adhesives, a subset of the present invention when they are composed in the proportions described herein.

It is a primary object of the present invention to provide a tissue crosslinking prepolymer which will form a mammalian tissue crosslinked bond.

It is an object of the present invention to provide a 1-part tissue bonding composition that bonds mammalian tissue together in one step.

It is another object of the present invention to achieve a catalytic amine by providing in the 1-part fomulation an excess of free polyisocyanate that is transformed to the amine by body fluids.

It is another object of the present invention to provide a prescription and means for the proper form of the polyol to be used in the present invention wherein the polyol should be multifunctional or branched.

It is another object of the present invention to provide prescriptions for the composition of the polyol that provide for hydrogel formation and absorbability.

It is one primary object of this invention to provide, through the composition of the adhesive, a sequence of chemical reactions that will ensure optimal tissue bonding. Namely, free polyisocyanates with their lower molecular weight and low viscosity will be present to bond first to tissue, thereby providing a strong link between tissue and the larger molecular weight of the polyisocyanate capped polyol. Those free polyisocyanates that are not bonded to tissue are converted to amines by fluids in and surrounding the tissue. These amines migrate into the bulk of the adhesive creating first links between the capped polyol and polyisocyanates bonded to tissue and second linking arms of the capped polyols.

It is another primary object of this invention to provide a biodegradable tissue adhesive. One novel feature of the present invention is that the structure of the adhesive is not broken down. Weak crosslinking provides dissolution of the adhesive. The implant swells and eventually goes into solution without actual breaking of the chemical bonds.

It is another object of the present invention to provide an absorbable tissue adhesive that does not sacrifice strength for degradability.

It is another object of the present invention to provide a biocompatible, non-absorbable tissue adhesive that remains biocompatible by providing resistance to chemical degradation.

BRIEF SUMMARY OF THE INVENTION

The present invention provides for a 1-part surgical adhesive capable of forming covalent bonds to mammalian body tissue and capable of forming a hydrogel comprised of body fluids. Successful formation of the tissue bond that is not absorbable requires certain unique features:

1. The polyol backbone of the present invention is a mixture of ethylene oxide and propylene oxide (EO/PO), preferably as a block polyol of between 2,000 and 20,000 MW. The block structure can be random or regular. The block structure should contain at least 10% PO, preferably 25%. The polyol should be multifunctional, preferably tri-functional. A tri-functional structure can be built by reacting together EO/PO diols of 800-5000 MW and a tri-functional linking agent such as trimethylol propane. The polyol should be liquid at room temperature. Polyols with multiple branched structure, such as star molecules, typically will result in adhesives which are too viscous. High viscosity prevents optimal contact between tissue and adhesive and slows the water curing process by impeding diffusion of water into the bulk adhesive.

2. The tri-functional polyol is capped with an aromatic diisocyanate such as toluene diisocyanate such that isocyanate-to-hydroxyl group ratio is greater than 1.5, and preferably between 1.5 and 3. Halogen diisocyanates are too reactive and produce unstable compositions and poor tissue bonding. Weakly reactive diisocyanates, such as lysine diisocyanate will not bond quickly to tissue.

3. The isocyanate concentration in the composition is preferably between 0.05 and 1.6 milliequivalents per gram in order to ensure complete capping of the polyol and to satisfy the requirement that an excess of free polyisocyanate be present in the final composition Successful formation of a tissue bond that is absorbable requires certain unique features:

1. All of the above except the polyol is substantially all EO and the fraction of polyol that is trifunctional is less than the fraction of the polyol that is PO.

In addition to the enhanced biocompatibility of hydrogel bond structures, further improvements in biocompatibility can be achieved by providing an excess aliphatic multi-functional isocyanate to serve as a scavenger for trace free amine created during the polymerization process.

Since compositions of the present invention are intended for medical use they must have certain properties specific to that industry. For example, none of the reactions required to form the adhesive should require a metallic catalyst. The final composition should have a solid-to-liquid transition temperature below 20° C. The viscosity of the final composition should be less than 20,000 cps, and preferably less than 10,000 cps. The final composition should contain no solvents or other components that are used only to reduce the viscosity of the adhesive. These components are lost to the body in the formation of the hydrogel and are not preferred. The pre-polymerized composition should be substantially dissolvable in water in an adhesive-to-water ratio of 10:1 to 20:1.

All of the isocyanate functionality in the form of free isocyanate and active capped ends of the polyol must be consumed by three reactions. Those reactions are: 1) bonds to tissue to activate the tissue, 2) bonds between activated tissue and polyol, and 3) bonds between terminated polyol.

The adhesive composition must be easily applied to tissue, requiring that it be 1-part, hydrophilic, useable at room temperature, stable during room temperature storage, stable during gamma or electron radiation up to 25 kgy. The extent of internal crosslinking during radiation sterilization should be less than 25% at 25 kgy. The adhesive composition should bond to tissue in less than 120 seconds.

Enhanced tissue penetration and faster bonding can be achieved by heating the adhesive. In general, chemical reaction rate halves with each 10° C. increase in adhesive temperature.

The present invention also comprises a method of establishing an organic hydrogel bond at a situs of living tissue comprising the steps of: pre-treating disparate portions of the living tissue with free polyisocyanate, body derived fluids, at lease one NCO-terminated hydrophilic polyol, derived from an organic polyisocyanate, and bonding or sealing the living tissue. The steps preferably occur as a result of contact between present invention and living tissue.

DETAILED DESCRIPTION OF THE INVENTION

The present invention relates to a 1-part surgical adhesive wherein covalent bonds are formed with body tissue and a hydrogel is formed of body fluids. However, the vast majority of NCO-terminated hydrophilic urethane prepolymers do not form such hydrogels. Urethane prepolymers are deemed hydrophilic if they incorporate in the urethane structure between 2 and 10% water. Such prepolymers are not effective as surgical adhesives since they are not hydrophilic enough and do not form hydrogels. Such prepolymers, when placed in an environment where the water exceeds 10% of the prepolymer volume polymerize internally without linking to tissue or fail to form a solid.

Consequently, the majority of hydrophilic polyether polyols can be excluded for use in the present invention. In particular, the polyol of choice is a tri-functional form of PE/PO block polymer. The ratio of PE to PO is critical to the formation of the hydrogel. The PE provides the necessary hydrophilic nature, and the PO provides hydrogel strength. For example, adhesives formed from pure PE tend to breakdown in the body and swell to 2 to 10 times their original volume within several hours.

Adhesives of highest reliability will be non-absorbable and contain 10 to 30% PO. Adhesives with greater than 30% PO will not form hydrogels comprising greater than 50% water by volume.

In certain medical applications an absorbable adhesive is desirable. The rate of absorption can be controlled by adjusting the amount of PO, typically about 10% for adhesives with a residence time of about 1-2 weeks.

Tri-functional PE/PO polyols can be prepared by reacting PE/PO diols of between 800 and 5,000 MW with a triol. There are many suitable triols: triethanolamine, trimethylolpropane, trimethyloethane and glycerol.

In the present invention, the prepared tri-functional PE/PO, between 2 to 4 hydroxyl groups, is reacted with polyisocyanate. For strong, fast tissue bonding, aromatic diisocyanate is preferably used. Toluene diisocyanate is a suitable aromatic diisocyanate, and 2,6-toluenediisocyanate is preferred. Commercially available mixtures of 2,4- and 2,6-toluenediisocyanate are suitable, but less biocompatible.

For adhesive tissue bulking compositions, aliphatic diisocyanate is preferably used Isophorone diisocyanate is a preferred aliphatic diisocyanate. Absorbable versions of the adhesive of the present invention can be formed by using either diisocyanate type.

Enough polyisocyanate must be provided so that the non-polymerized polyisocyanate accounts for less than 5% (v/v) and greater than 1% of the adhesive. This excess ensures a covalent bond is formed between the adhesive and the body tissue. Other adhesives lack excess polyisocyanate and form a bond by infiltrating tissue structures and solidifying within these structures forming mechanical bonds that can be disrupted by stress and polymer swelling.

Since the terminated isocyanate and excess isocyanate serve two different functions, the polyol may be terminated with a weaker reacting isocyanate, such as p-phenylene diisocyanate or lysine diisocyanate. However, for the adhesive to bond to tissue effectively an excess of TDI (Toluene Diisocyanate) or IPDI (Isophorone Diisocyanate) or similarly reactive diisocyanate should be added secondarily to the capped polyol. In this case, one of the isocyanates can be a halogen diisocyanate.

Additionally, there may be more than one isocyanate terminated polyol. When the more aggressively reactive aromatic isocyanate terminated polyols polymerize, some of the excess isocyanate may be excluded from the polymerization reaction and reside as free amines in the formed polymer. If a stoichiometric amount of aliphatic isocyanate terminated polyol is present, these will not polymerize as aggressively providing greater opportunity for the formed aromatic amine to be incorporated in the polymerization process by urea addition products. Even if these addition products do not incorporate into the bulk polymerized structure, they are considerably more biocompatible than free aromatic amines.

When a minimal amount of aliphatic terminated polyol in the 1-part adhesive composition is desired, the amount is preferably in the range 0.01 to 0.05 by volume. More generally, matching the number of aliphatic terminated polyol to the number of free isocyanate is desired.

In the application of the adhesive of the present invention to body tissue, the adhesive may be applied conventionally with a standard syringe fitted with a suitable gauge needle. The syringe can be heated in a warm water bath to further decrease adhesive viscosity. Hemostasis can be achieved by applying the adhesive to a suitable substrate such as meshes made of polyester, polypropylene, oxidized cellulose, collagen, or like materials. Cured sheets of the adhesive can be bonded to tissue by applying a thin layer of uncured adhesive thereon. Various grafts and tissue anastomoses can be sealed and/or joined using the adhesive. The adhesive can coat standard sutured anastomoses rendering them hemostatic or the adhesive can be used to buttress sutures or mechanical applier devices such as staples. The adhesive bonds to any material containing water, and will mechanically bond porous or woven materials. Applicable tissues include blood vessels, lung, heart, esophagus, stomach, and skin. The adhesive can also be used to augment tissue my injection into tissue. The adhesive can be used to deliver therapeutics such as water soluble drugs, radiation sources, and chemo therapies.

EXAMPLES

NCO-terminated prepolymers were prepared by mixing each deionized, dried polyether polyol with each polyisocyanate and reacting them at 60° C. for 6 hours to 3 days.

Example 1

A tri-functional polyether polyol was formed by reacting a PE/PO 80:20 random copolymer having an average MW of 2600 with BASF Luparnate T80-1 (80:20 2,4- and 2,6-toluenediisocyanate) and trimethylolpropane (1-5%) to obtain a NCO-terminated hydrophilic prepolymer having a free NCO content of 3%.

Example 2

A tri-functional polyether polyol was formed by reacting a PE/PO 80:20 random copolymer having an average MW of 2600 with IPDI and trimethylolpropane (1-5%) to obtain a NCO-terminated hydrophilic prepolymer having a free NCO content of 1.5%.

Example 3

A tri-functional polyether polyol was formed by reacting a PE/PO 80:20 random copolymer having an average MW of 2600 (30-20%) and polyethylene glycol of 1000 MW (30-50%) with IPDI (23-39%) and trimethylolpropane (1-5%) to obtain a NCO-terminated hydrophilic prepolymer having a free NCO content of 1.5%.

Example 4

A tri-functional polyether polyol was formed by reacting a PE/PO 80:20 random copolymer having an average MW of 2600 (30-20%) and polyethylene glycol of 1000 MW (30-50%) with BASF Luparnate T80-1 (80:20 2,4- and 2,6-toluenediisocyanate) (23-39%) and trimethylolpropane (1-5%) to obtain a NCO-terminated hydrophilic prepolymer having a free NCO content of 1.5%.

Example 5

A tri-functional polyether polyol was formed by reacting a PE/PO 80:20 random copolymer having an average MW of 2600 (5-10%) and polyethylene glycol of 1000 MW (45-70%) with BASF Luparnate T80-1 (80:20 2,4- and 2,6-toluenediisocyanate) (23-39%) and trimethylolpropane (1-5%) to obtain a NCO-terminated hydrophilic prepolymer having a free NCO content of 1.5%.

Example 6

A tri-functional polyether polyol (marketed as) Veranol CP 1421 average MW of 1421 was reacted with BASF Luparnate T80-1 (80:20 2,4- and 2,6-toluenediisocyanate) (23-39%) to obtain a NCO-terminated hydrophilic prepolymer having a free NCO content of 3.1%.

Example 7

A tri-functional polyether polyol Veranol CP 1421 average MW of 1421 was reacted with (commercially available) BASF Luparnate T80-1 (80:20 2,4- and 2,6-toluenediisocyanate) (23-39%) to obtain a NCO-terminated hydrophilic prepolymer having a free NCO content of 3.1%.

The invention thus comprises a biocompatible tissue-bonding adhesive composition comprising: a polyol of functionality N, wherein the polyol being terminated with at least one polyisocyanate in solution with at least (N−1)% of said solution comprising free polyisocyanate. N may be in the range 1.5-8. The polyol may be a branched polypropylene/polyethyle-ne oxide copolymer. The polypropylene/polyethylene oxide copolymer contains polypropylene oxide in a range of about 10% and 30%. The polypropylene/polyethylene oxide copolymer may contain no more than 10% polypropylene oxide. The polyisocyanate may be comprised of a 80:20 mixture of 2,4-toluene diisocyanate and 2,6-toluene diisocyanate. The polyisocyanate may consist of 2,6-toluene diisocyanate only. The polyisocyanate may consist of isophorone diisocyanate. The polyisocyanate may consist of an 80:20 mixture of 2,4-toluene diisocyanate and 2,6-toluene diisocyanate and 3% of the composition is free polyisocyanate. The polyisocyanate may consist of isophorone diisocyanate and about 1.5% of the composition consists of free polyisocyanate. The composition may be comprised of two polyisocyanates and wherein one of the polyisocyanates comprises a free isocyanate B as an aromatic polyisocyanate and the other of the polyisocyanates comprises an aliphatic isocyanate A which is used to endcap said copolymer. The free isocyanate B may convert to an amine faster than the isocyanate A. The free isocyanate B may be more reactive with nitrogenous substances than the isocyanate A. The free isocyanate B may be of lower viscosity than the isocyanate A.

The invention may also comprise a biocompatible adhesive composition comprising of at least two branched polyols of functionality 1.5-8, the polyols being terminated with at least one polyisocyanate in solution with at least 1% of said solution comprising free polyisocyanate. At least one of the polyols may be a branched polypropylene/polyethylene oxide copolymer. One of the branched polyols may consist of a copolymer of less than 10% polypropylene oxide and another of the branched polyols may comprise a copolymer consisting of between 10 and 30% polypropylene oxide, both of the copolymers of functionality 1.5-8, the copolymers being terminated with at least one polyisocyanate in solution with at least 1% of the solution comprising free polyisocyanate. One of the polyol copolymers may consist of 5% polypropylene oxide and the other of the polyol copolymers may consist of 25% polypropylene oxide. The copolymer having a lesser functionality may comprise at least 25% by molecular number of the total copolymer component. One of the copolymers may have functionality less than the other of the copolymers. One of the copolymers may have functionality 2 and the other of the copolymers have functionality 3. The copolymer of lesser functionality may be less than 25% by molecular number of the total copolymer component. One polyol may be terminated with a polyisocyanate with water reactivity R1 and another polyol is terminated with a polyisocyanate with water reactivity R2, where R1>R2, both of the terminated polyols of functionality 1.5-8, the terminated polyols being in solution with at least 1% of the solution comprising free polyisocyanate of reactivity R1. One of the polyols may be terminated with an aromatic polyisocyanate and another of the polyols may be terminated with an aliphatic polyisocyanate, both of the polyols of functionality 1.5-8, the terminated polymers in solution with at least 1% of the solution comprising free polyisocyanate. The free polyisocyanate may be aromatic. The free polyisocyanate may be comprised of toluene diisocyanate. The free polyisocyanate may consist of isomer 2,6-toluene diisocyanate. The composition may eliminate amines during polymerization induced by water or proteins where the less reactive isocyanate capped polyol is present in stoichiometric amounts. The isocyanate used to cap said polyol may be comprised of isophorone diisocyanate. The polyol may be 75% polyethylene oxide and 25% polypropylene oxide.

The invention also comprises a method for covalent bonding of tissue, which comprises: applying to the tissue a 1-part surgical adhesive consisting essentially of at least one NCO-terminated branched polymer, derived from at least one organic polyisocyanate and at least 1% unreacted polyisocyanate wherein the polymerization proceeds by the following time-ordered steps: free polyisocyanate bonds to tissue, said free polyisocyanate converts to a polyamine and links the NCO-terminated branched polymer to the tissue bonded polyisocyanate; the free polyisocyanate converts to polyamine and links the branched polymer to the other same polymers. The polymer may comprise a poly-propylene/polyethylene copolymer.

The invention may also comprise a method for covalent bonding of tissue, which comprises: applying to the tissue a 1-part surgical adhesive consisting essentially of a NCO-terminated branched polymer, derived from an organic polyisocyanate A and at least 1% unreacted polyisocyanate B wherein polyisocyanate B is more reactive with amine groups than polyisocyanate A and wherein the polymerization proceeds by the following time-ordered steps: the polyisocyanate B bonds to tissue, the free polyisocyanate B converts to a polyamine and links said polyisocyanate A-terminated branched polymer to the tissue bonded polyisocyanate B, the free polyisocyanate B converts to polyamine and links the branched polymer to the other same polymers. The polymer may comprise a polypro-pylene/polyethylene copolymer.

The invention may also comprise a method for covalent bonding of tissue, which comprises: applying thereto a 1-part surgical adhesive consisting essentially of a NCO-terminated branched polymer, derived from an aromatic polyisocyanate A and at least 1% unreacted polyisocyanate A and a NCO-terminated branched polymer, derived from an aliphatic polyisocyanate B, wherein the polymerization proceeds by the following time-ordered steps: the polyisocyanate A bonds to tissue, the free polyisocyanate A converts to a polyamine and links the polyisocyanate A-terminated branched polymer to the tissue bonded polyisocyanate A, the free polyisocyanate A converts to polyamine and links the polyisocyanate A terminated branched polymers to the other polyisocyanate A terminated branched polymers, the free polyisocyanate A converts to polyamine and links to polyisocyanate B terminated branched polymers. The method may include converting the free polyisocyanate A to polyamine; and linking polyisocyanate B terminated branch polymers to other NCO terminated branched polymers. The polymer may be a copolymer of polyethylene oxide and polypropylene oxide.

The invention may also include a method for covalent bonding of tissue, which comprises: applying thereto a 1-part surgical adhesive consisting of two NCO-terminated branched polypropylene/polyethylene oxide copolymers, wherein copolymer A is at most 10% polypropylene oxide and copolymer B is between 10% and 30% polypropylene oxide, derived from an organic polyisocyanate and at least 1% unreacted polyisocyanate wherein the polymerization proceeds by the following time-ordered steps: the free polyisocyanate bonds to tissue, the free polyisocyanate converts to a polyamine and links both polypropylene/polyethylene oxide copolymers to the tissue bonded polyisocyanate, the free polyisocyanate converts to polyamine and links the branched polypro-pylene/polyethylene oxide copolymers to the other same polymers, and polymerized copolymer A swells within the formed polymer matrix and causes degradation of the formed matrix.

The invention may also comprise a method for covalent bonding of tissue, which comprises: applying thereto a 1-part surgical adhesive consisting of two NCO-terminated branched polypropylene/polyethylene oxide copolymers, wherein copolymer A is at most 10% polypropylene oxide and copolymer B is between 10% and 30% polypropylene oxide, wherein copolymer A is substantially more viscous than copolymer B, derived from an organic polyisocyanate and at least 1% unreacted polyisocyanate wherein the polymerization proceeds by the following time-ordered steps: the free polyisocyanate bonds to tissue, the free polyisocyanate converts to a polyamine and links copolymer B preferentially to the tissue bonded polyisocyanate, the free polyisocyanate converts to polyamine and links the branched polypropylene/polyethylene oxide copolymers to the other same polymers, the polymerized copolymer A swells within the formed polymer matrix and causes degradation of the formed matrix, and polymerized copolymer B does not swell at the tissue/matrix interface and does not cause tissue bond degradation.

What is claimed is:

1. A biocompatible composition comprising
a cyanate-terminated hydrophilic prepolymer comprising:
   a copolymer comprising polyether monomers and from 10% to 30% of propylene oxide monomers;
   from 23 to 39 wt. % of at least one polyisocyanate selected from the group consisting of 2,4-touluene diisocyanate, 2,6-toluene diisoscyanate, and isophorone diisocyanate; and
   from 1 to 5 wt. % of trimethylolpopane;
   wherein the prepolymer is a liquid, water-soluble, and comprises from 1.5 to 5% free polyisocyanate content.

2. The biocompatible composition of claim 1 wherein the prepolymer is dissolvable in water at a prepolymer to water ratio of 10:1 to 20:1.

3. The biocompatible composition of claim 1 wherein the prepolymer has a viscosity less than 20,000 cps.

4. The biocompatible composition of claim 1 wherein the prepolymer has a viscosity less than 10,000 cps.

5. The biocompatible composition of claim 1 wherein the prepolymer has a solid to liquid transition temperature of less than 20° C.

6. The biocompatible composition of claim 1 wherein the copolymer of polyether monomers comprises PE/PO in a ratio of 80:20.

7. The biocompatible composition of claim 1 wherein the copolymer of polyether monomers is a random copolymer.

8. The biocompatible composition of claim 1 wherein the copolymer has a molecular weight of from 800 to 5,000.

9. The biocompatible composition as recited in claim 1, wherein said at least one polyisocyanate is 2,6-toluene diisocyanate.

10. The biocompatible composition as recited in claim 1, wherein said at least one polyisocyanate is isophorone diisocyanate.

11. The biocompatible composition as recited in claim 1, wherein said at least one polyisocyanate is an 80:20 mixture of 2,4-toluene diisocyanate and 2,6-toluene diisocyanate.

12. The biocompatible composition as recited in claim 1, further comprising an aqueous solution, wherein the composition has a prepolymer to aqueous solution ratio of 10:1 to 20:1.

13. The biocompatible composition as recited in claim 1 wherein the composition has a solid-to-liquid transition temperature below 20° C.

14. The biocompatible composition as recited in claim 1 wherein the composition has a viscosity of less than 20,000 cps.

15. The biocompatible composition as recited in claim 1 wherein the copolymer has a molecular weight of 800 to 5000.

* * * * *